United States Patent [19]

Eves

[11] Patent Number: 5,372,273

[45] Date of Patent: Dec. 13, 1994

[54] INCLINABLE COMPARTMENTED STORAGE CONTAINER

[76] Inventor: Mark G. Eves, 150 Holstrom Cir., Novato, Calif. 94947

[21] Appl. No.: 184,571

[22] Filed: Jan. 21, 1994

[51] Int. Cl.⁵ .............................................. B65D 5/48
[52] U.S. Cl. .................................. 220/507; 206/45; 206/45.24
[58] Field of Search .............. 220/507, 629; 206/44, 206/45, 45.13, 45.14, 45.18, 45.24

[56] References Cited

U.S. PATENT DOCUMENTS

| | | | |
|---|---|---|---|
| 457,598 | 2/1891 | Briggs | 206/45 X |
| 897,002 | 8/1908 | Merritt | 206/45 |
| 970,454 | 9/1910 | McKenzie | 206/45 |
| 1,308,949 | 7/1919 | Harris et al. | 206/45.24 |
| 4,753,341 | 6/1988 | McIntyre | 206/45 |

*Primary Examiner*—Steven M. Pollard
*Attorney, Agent, or Firm*—Claude A. S. Hamrick

[57] ABSTRACT

An inclinable compartmented storage container including a flat, generally trapezoidally-shaped bottom portion having two parallel peripheral edges of non-equal length, and two non-parallel peripheral edges of equal length. The parallel edges are relatively disposed such that a line segment drawn between the respective midpoints associated with each parallel edge perpendicularly intersects each parallel edge. Upstanding sidewall portions extend upwards from, and in a substantially perpendicular manner, each of the non-parallel edges. Also, upstanding endwall portions extend generally obliquely upwards from each of the parallel edges. A means for inclining the container above a top surface of a work table is attached to the bottom portion and is disposed adjacent to one of the parallel but non-equal edges. Two longitudinal dividers are disposed within the container and divide the interior of the container into three columnar sections. The longitudinal dividers are attached to each of the endwall portions and extend perpendicularly upwards from the bottom portion. A plurality of transverse dividers are attached between each of the longitudinal dividers, or between a longitudinal divider and an adjacent sidewall portion thereby dividing each columnar section into a plurality of non-rectangular quadrilaterally-shaped compartments of unequal volumes.

12 Claims, 5 Drawing Sheets

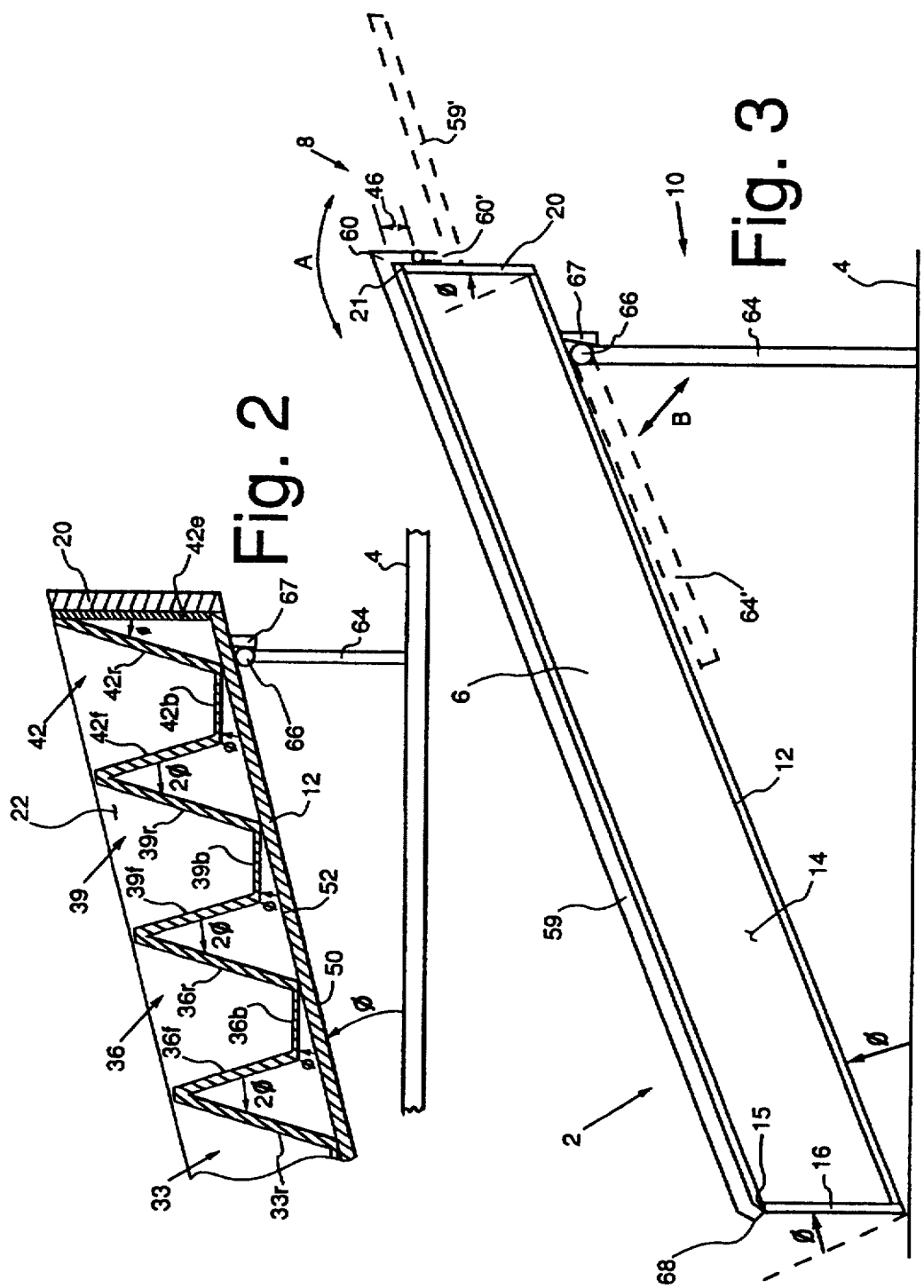

INCLINABLE COMPARTMENTED STORAGE CONTAINER

BACKGROUND OF THE INVENTION

1. Field of the Invention

This invention relates generally to compartmented containers, and more particularly to an inclinable generally trapezoidally-shaped compartmented storage container.

2. Brief Description of the Prior Art

There are many applications which require the storage of a wide number of items such as granular powders and the like in a single tray or compartmented storage container. Furthermore, in many of these applications, a craftsman or technician is required to repeatedly access and retrieve substances stored within the various compartments of the container. For example, in the art of making dental appliances such as crowns and bridges etc., a large number of dry porcelain powders are available to make a single appliance. Each powder is contained in a compartment formed in the container, and several powders (i.e. compartments) must be accessed and retrieved during the manufacture of a single appliance. It will be appreciated that the faster the access and retrieval time the faster the overall productivity of the craftsman. Therefore, in order to increase productivity the stored substances, i.e. the compartments, must be within convenient reach of the user.

There are several prior art devices disclosed that can be adapted to contain substances such as dry porcelain powders. For example, U.S. Pat. No. 5,203,450 (issued to Benetti) discloses a combination display and packaging container which includes a plurality of spaced-apart depressions that can be adapted to hold the powder-like substances. Other devices, e.g. U.S. Pat. No. 4,648,524 issued to Ackerman, U.S. Pat. No. 4,572,367 issued to Uslar and U.S. Pat. No. 4,887,790 issued to Wilkinson et al., disclose compartmented trays or containers wherein the compartments may be adapted for storing and dispensing powder-like materials.

Other prior art devices, for example U.S. Pat. No. 2,944,696 issued to Effgen, U.S. Pat. No. 4,948,368 issued to Knotscher, and U.S. Pat. No. 4,180,159 issued to Tanaka all disclose trays wherein a powder-like material may be wetted, or, in the case of Effgen (U.S. Pat. No. 2,944,696) an item is immersed in a fluid and the fluid is subsequently drained away. Thus, these devices are not suitable for storing and/or dispensing dry powder-like material.

Although the prior art discloses compartmented storage containers, there are numerous shortcomings associated width these disclosed containers that makes them unsuitable for manufacturing applications demanding quick access to large numbers of powder-like substances, i.e. large numbers of storage compartments.

For example, all of the containers or trays disclosed above are generally rectangular in shape, i.e. opposing sides of the trays are equal in length and disposed in parallel spaced-apart relationship to one another. When large numbers of substances, i.e. compartments, must be accessed, a single rectangularly-shaped container must be large enough to accommodate all the stored substances. Thus, some compartments of the container will be inconvenient and difficult to reach, and the productivity of the user will consequently be reduced. As an alternative, a plurality of compartmented rectangularly-shaped containers could be used. However, because of their rectangular shape, the plurality of containers cannot be arranged in a convenient and efficient configuration around a centrally disposed user. As with the single container situation, the user will not have quick and equal access to all compartments of every storage container.

Furthermore, the storage containers disclosed in the prior art are disposed in a flat or non-inclined manner atop the top surface of a work table. It will be appreciated that if the storage container includes a large number of storage compartments then some compartments will be relatively farther away from the user than other compartments. In a large system having a large number of compartments, the productivity of the user will be severely reduced if equal access to all compartments of all storage containers is not provided.

Thus, there is a need to provide a compartmented container for containing substances that does not possess the shortcomings of the containers used in the prior art.

SUMMARY OF THE PRESENT INVENTION

It is an object of the present invention to provide an improved compartmented storage container for containing powder-like substances and the like.

It is a further object of the present invention to provide an improved compartmented storage container that is inclinable so as to be disposed at an angle relative to the top surface of a work table.

It is another object of the present invention to provide an inclinable compartmented storage container that is generally trapezoidally-shaped.

It is still a further object of the present invention to provide an inclinable trapezoidally-shaped compartmented storage container that can be adjoined to another like storage container so as to form an adjoined inclinable compartmented container.

It is still another object of the present invention to provide a plurality of adjoined inclinable compartmented containers that can be arranged in a generally semi-circular fashion around a technician or craftsman.

Briefly, an inclinable compartmented storage container includes a flat, generally trapezoidally-shaped bottom portion having two parallel peripheral edges of non-equal length, and two non-parallel peripheral edges of equal length. The parallel edges are relatively disposed such that a line segment drawn between the respective midpoints associated with each parallel edge perpendicularly intersects each parallel edge. Upstanding sidewall portions extend upwards from, and in a substantially perpendicular manner, each of the non-parallel edges. Also, upstanding endwall portions extend generally obliquely upwards from each of the parallel edges. A means for inclining the container above a top surface of a work table is attached to the bottom portion and is disposed adjacent to one of the parallel but non-equal edges.

Two longitudinal dividers are disposed within the container and divide the interior of the container into three columnar sections. The longitudinal dividers are attached to each of the endwall portions and extend perpendicularly upwards from the bottom portion.

A plurality of transverse dividers are attached between each of the longitudinal dividers, or between a longitudinal divider and an adjacent sidewall portion thereby dividing each columnar section into a plurality of non-rectangular quadrilaterally-shaped compartments of unequal volumes.

Among the advantages of the present invention are that the storage container is inclinable, thereby reducing the distance from the user to the rear-most compartments and, thus, providing greater user access to all compartments of the container.

Another advantage of the present invention is that the storage container is generally trapezoidally-shaped thereby allowing a plurality of like containers to be efficiently arranged, in a semi-circular manner, about a user; thus, the user is provided with more efficient access to all compartments of all containers thereby increasing productivity.

A further advantage of the present invention is that because of the generally trapezoidal shape of the storage container, the individual compartments have unequal storage volumes, and, thus, more readily required substances can be stored in larger volume compartments.

IN THE DRAWING

FIG. 2 is a sectional view of a portion of the compartmented storage container taken along the line 2—2 of FIG. 1;

FIG. 3 is a side elevation view showing the inclinable compartmented storage container of the present invention, further illustrating a container lid covering the tray portion of the container, and a foldable support member downwardly extended to incline the container with respect to the surface of the table;

DETAILED DESCRIPTION OF THE PREFERRED EMBODIMENT

Figure 1:
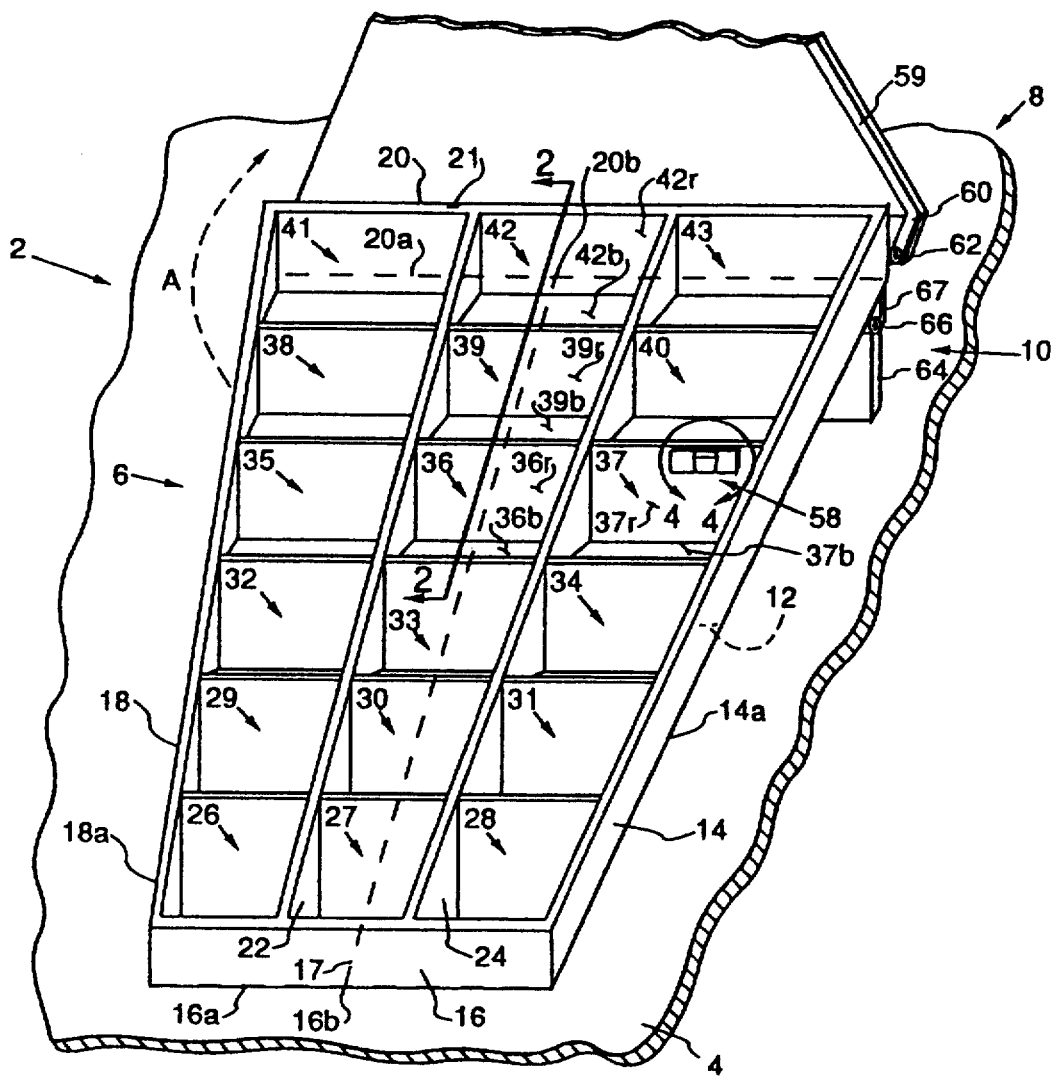
FIG. 1 is a perspective view illustrating an inclinable compartmented storage container of the present invention, the container being disposed on a top surface of a table.

FIG. 1 is a perspective view illustrating an inclinable compartmented storage container 2 disposed atop a surface 4 of a work table (not shown). FIG. 2 is a partial sectional view of the container 2 taken along a line 2—2 of FIG. 1. Viewing FIG. 1 and FIG. 2 together, the storage container 2 includes a compartmented tray 6, a rotatable lid 8 for covering the tray 6, and an inclining means or rotatable support member 10. When the inclining means or support member 10 is rotated to a downwardly extending position from the tray 6, as illustrated, the tray 6 is inclined by an angle $\emptyset$ relative to (i.e. "above") the surface 4. The typical value for $\emptyset$ is from 10 to 20 degrees.

The tray 6 includes a flat bottom portion 12 that is generally trapezoidally-shaped. The portion 12 has two parallel peripheral edges of non-equal length (indicated by dashed lines 16a and 20a), and two non-parallel peripheral edges 14a, 18a of equal length. The parallel edges 16a, 20a are relatively disposed such that a line segment 17 drawn between the respective midpoints 16b, 20b associated with each parallel edge 16a, 20a perpendicularly intersects each parallel edge 16a, 20a.

Four upstanding portions 14, 16, 18 and 20 vertically extend from the outer edges 14a, 16a, 18a, 20a of the portion 12. For purposes of definition, the portion 16 is disposed at the "front" of the tray 6, the portion 20 is disposed at the "rear," and the portions 14 and 18 are disposed at the "sides" of the tray 6. The upstanding portions 14, 16, 18, 20 are elongated, and substantially flat. The portions 14 and 18 are generally parallelogram shaped and have generally equal lengths but are disposed in a non-parallel relation; in contrast, the portions 16 and 20 are generally rectangularly shaped, unequal in length, and are disposed in a parallel relationship. The portions 16 and 20, as can best be seen in FIG. 2, extend obliquely upwards from the portion 12, by an angle $\emptyset$. That is, when the tray 6 is disposed flush atop the surface 4, the portions 16 and 20 are canted by the angle $\emptyset$ from the vertical. Note further, that when the tray 6 is inclined, as illustrated in FIG. 2, the portion 16, 20 are disposed perpendicularly to the surface 4. The portions 14 and 18 are disposed perpendicularly to the surface 4, whether or not the tray 6 is inclined.

A plurality of longitudinal dividers 22 and 24 are disposed in the tray 6 and divide it into three columnar sections or compartments. The dividers 22, 24 are elongated flat, and substantially parallelogram shaped plates and are each attached at one end to the portion 20 and at the other end to the upstanding portion 16. Also, the dividers 22, 24 are shorter in length than the portions 14, 18. The dividers 22, 24 are equal in length but are disposed in a non-parallel relation, such that the tray 6 gradually tapers in width from the rear to the front because of the relative orientation of the portions 14, 18, and the dividers 22, 24.

A plurality of transverse dividers further divide the tray 6 into a plurality of quadrilaterally shaped compartments 26–43. It will be noted, that the individual compartments 26–43 have unequal volumes because of the non-parallel relationship between the portions 14 and 18, and the dividers 22 and 24. Also each compartment may have a compartment label or identifying means 58 affixed to an upstanding wall thereof to identify the substance stored therein.

The following discussion describes a single compartment and its constituent members. However, it will be appreciated that the description of one compartment is applicable to the other compartments. Each compartment includes a compartment base member, an inclined transverse front divider, and an inclined transverse rear divider. For example, with respect to a compartment 36, there is an inclined transverse rear divider or wall portion 36r, an inclined transverse front divider or wall portion 36f, and a compartment base member 36b. Similarly, a compartment 39 (FIG. 2) includes a rear divider or wal portion 39r, a front divider or wall portion 39f, and a base member 39b.

In the preferred embodiment, the tray 6, and its constituent upstanding portions 14, 16, 18, 20, and longitudinal and transverse dividers are cast or molded as one integral piece. In this manner, the dividers 36f, 36r, and the base member 36b are joined together such that they form, in cross-section, a generally U-shape (FIG. 2). It should be noted that the front divider of a compartment is attached to the rear divider of the immediately forward compartment such that the two dividers form an inverted "V". For example, the divider 39f of compartment 39 is attached to the divider 36r of the compartment immediately forward of compartment 39, i.e. compartment 36, to form an inverted "V" shape.

When the tray 6 is flush atop the surface 4, the respective base members of each of the compartments, e.g. 36b, 39b, 42b, are inclined by the angle $\emptyset$ from the surface 4. However, when the tray 6 is inclined above the surface 4, the base members are disposed substantially parallel to the surface 4.

When the tray 6 is inclined with respect to the surface 4, the rear dividers of each compartment, e.g. 33r, 36r, 39r, 42r, are inclined by an angle $\emptyset$ with respect to a line perpendicular to the surface 4. In this manner, when the tray 6 is inclined, a craftsman or technician may easily observe the compartment label 58 that may be affixed to the rear divider of a compartment to readily identify the substance stored therein. When the tray 6 is disposed flat atop the surface 4, the inclined members are tilted back by an angle $2\emptyset$ from vertical.

In the preferred embodiment, the tray 6, and its constituent upstanding portions 14, 16, 18, 20, longitudinal dividers 22, 24, and transverse dividers, e.g. 36f, 36r, and base member 36b are cast or molded as one integral piece.

In the alternative, the portion 12, the upstanding portions 14-20, the longitudinal dividers 22, 24, and the transverse dividers, e.g. 36f, 36r, and base member 36b could be individual pieces and attached to each other by gluing or by other methods known in the art. It should be noted that if individual pieces are joined together to form the transverse dividers, a caulking type material should be used at the joints between the dividers to provide a contoured surface that facilitates the removal of powders or other fine granular substances from a compartment. It will be appreciated that a variety of configurations could be utilized to the form the joints between adjacent pieces, e.g. butt-joints, overlapping joints, or tongue-in-groove style joints.

Referring now to FIG. 3 which is a side elevation view of the container 2 having the inclining means or rotatable support member 10 and the lid 8. The lid 8 includes a tray covering portion 59, a dogleg portion 60, and a hinge 62 attached to the outer surface 23 of the upstanding portion 20. As shown, in dashed lines 59' and 60' the lid 8 can be rotated in the direction of an arrow A so as to uncover the tray 6 and the compartments therein. The hinge 62 is of a design common in the art. In the preferred embodiment, the hinge 62 is formed integral to the surface 23 of the portion 12. In an alternate embodiment, the hinge 62 may be an individual piece, and attached to the surface 23 in any manner well-known in the art. The tray covering portion 59 (as can be partially seen in FIG. 1) is shaped so as to generally correspond to the shade of the bottom portion 12, and thereby cover the tray 6 with minimum overhang. A protruding member 68 extending downwardly from the tip of the lid covering portion 59 contacts the top edge 15 of the portion 16. The dogleg portion 60 allows the hinge 62 to be offset by a distance 46 from a top surface 21 of the portion 20.

In alternate embodiments, the hinge 62 could be located adjacent the top surface 21 and the dogleg portion 60 could be eliminated from the tray covering portion 59. Also, the protruding member 68 could be eliminated, and the covering portion 59 could be engaged in flush contact atop the tray.

The inclining means or foldable support member 10 includes a vertical member 64, a hinge joint 66, and a stop 57. The hinge 66 is of a design known in the art, and is either integral with the portion 12 or is an individual piece that is attached to the portion 12 in any manner known in the art. The vertical member 64 is an elongated generally rectangular-shaped flat plate that generally extends along the entire width of the portion 12. The hinge 66 is disposed on the bottom of the portion 12 and the member 64 is sized such that when the member 64 is downwardly extended, as illustrated, the tray 6 is inclined at an angle $\emptyset$ from the surface 4. The value of the angle $\emptyset$ ranges from 10-20 degrees. As shown in dashed lines 64' the vertical member 64 can be rotated in the direction of an arrow B such that the container 2 can be disposed generally flush onto the surface 4. The stop 67 is attached to the portion 12 and disposed relative to the member 64 so as to prevent the member 64 from rotating beyond the vertical.

Figure 4:
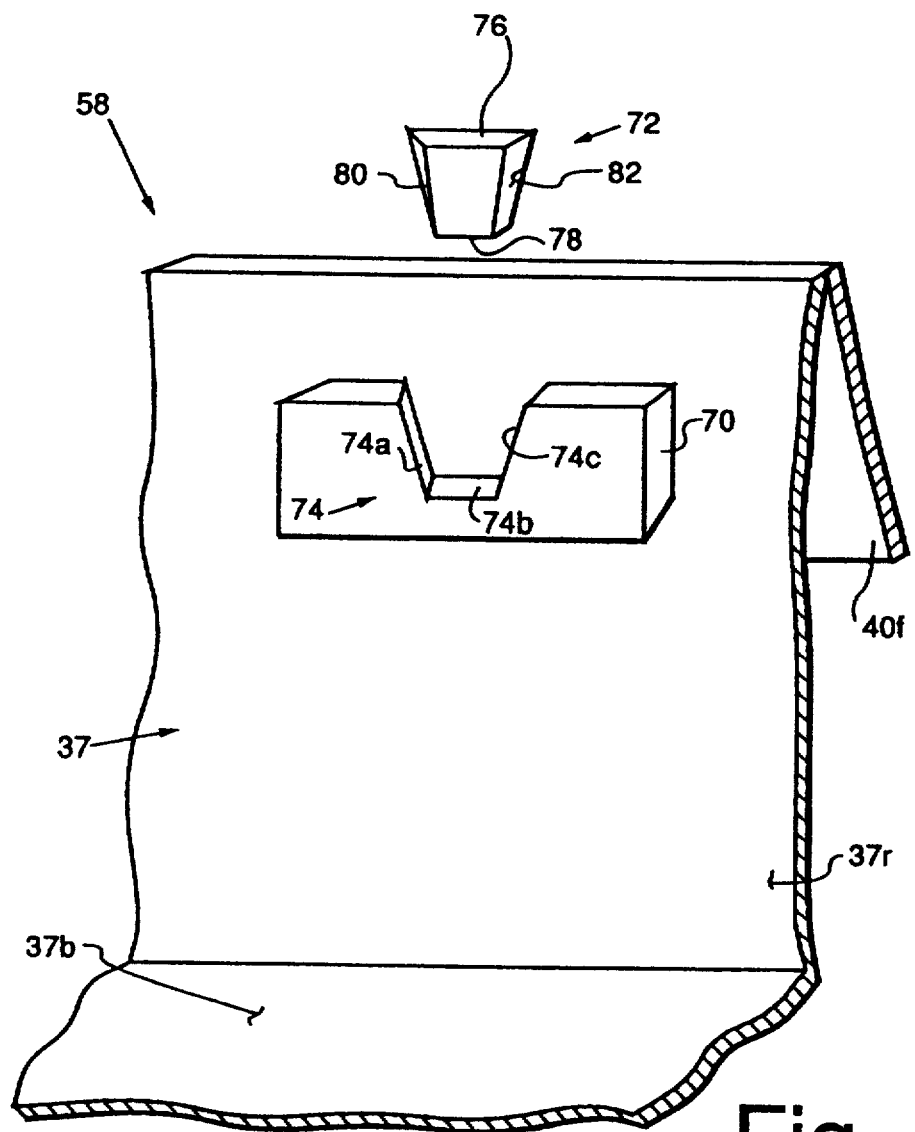
FIG. 4 is an enlarged perspective view depicting of the region 4—4 of FIG. 1.

FIG. 4 is an enlarged perspective view illustrating a portion of a compartment 37 of the tray 6. More specifically, the figure illustrates details of the identifying means or compartment label 58 which is affixed to an inclined rear transverse divider 37r of the compartment 37. The compartment label 58 includes a base member 70 and a label means or identification marker 72. The base member 70 is attached to the rear divider 37r of the compartment 37 by gluing or some other method known in the art. The member 70 includes a notch 74 for receiving the label means or identification marker 72. The notch 74 is shaped so as to receive the correspondingly shaped marker 72 that is slidably wedged therein. That is, the notch 74 includes inclined surfaces 74a, 74c, and a horizontal surface 74b. The marker 72 includes two inclined surfaces 82 and 80, and two horizontal surfaces 78 and 76. In this manner, the identification marker 72 may be moved vertically downward and slidably wedged into the notch 74. It will be appreciated that although an identifying means or compartment label 58 for compartment 37 is shown, a similar identifying means could be disposed in any other compartments. The label means or marker 72 can be a color sample to identify the color of the substance stored within the compartment, or it may carry some other description of the contents of the compartment, etc.

Figure 5:
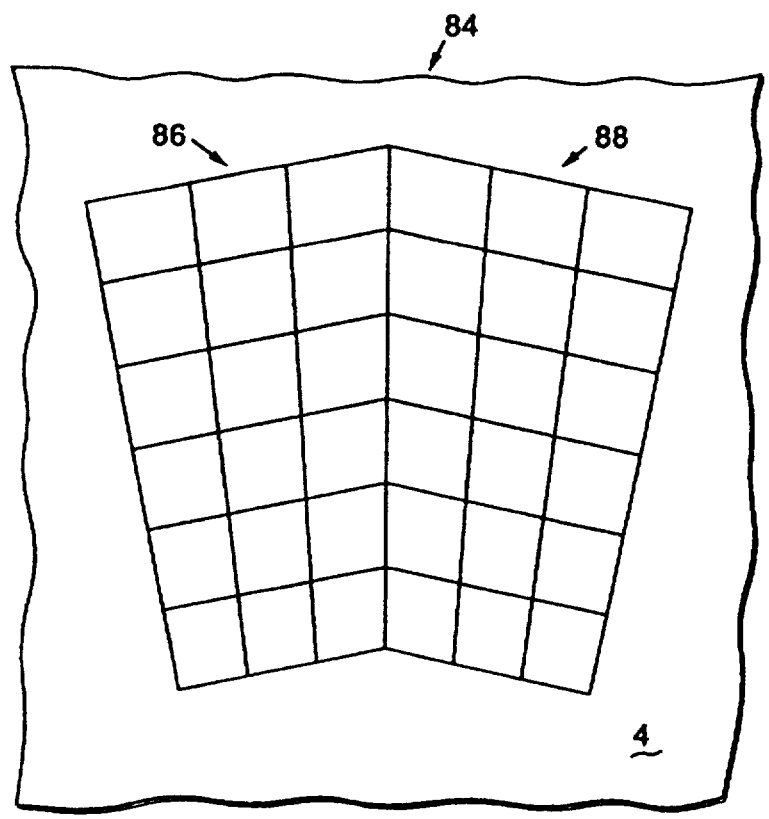
FIG. 5 is a plan view illustrating two inclinable compartmented storage containers adjoined to one another.
Figure 6:
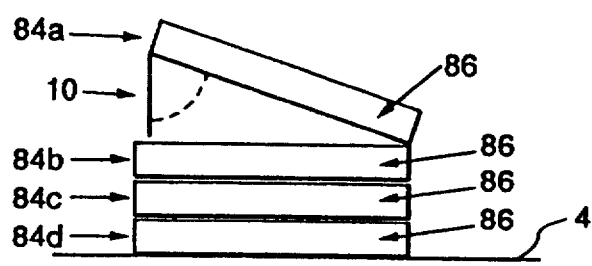
FIG. 6 is a side elevation view illustrating a plurality of adjoined storage containers illustrated in FIG. 5 stacked one atop the other.

FIGS. 5 and 6 show alternate embodiments of the inclinable compartmented storage container of the present invention. In this embodiment, an individual inclinable compartmented storage container 86 generally of the type similar to the container 2 (FIGS. 1-4) is joined to a like container 88 to form an adjoined inclinable storage container 84. The containers 86 and 88 may be attached together by gluing or by any other method well-known in the art. As illustrated in FIG. 6, adjoined inclinable storage containers 84a-84d may be stacked one upon the other to compactly store or more efficiently transport the containers.

Figure 7:
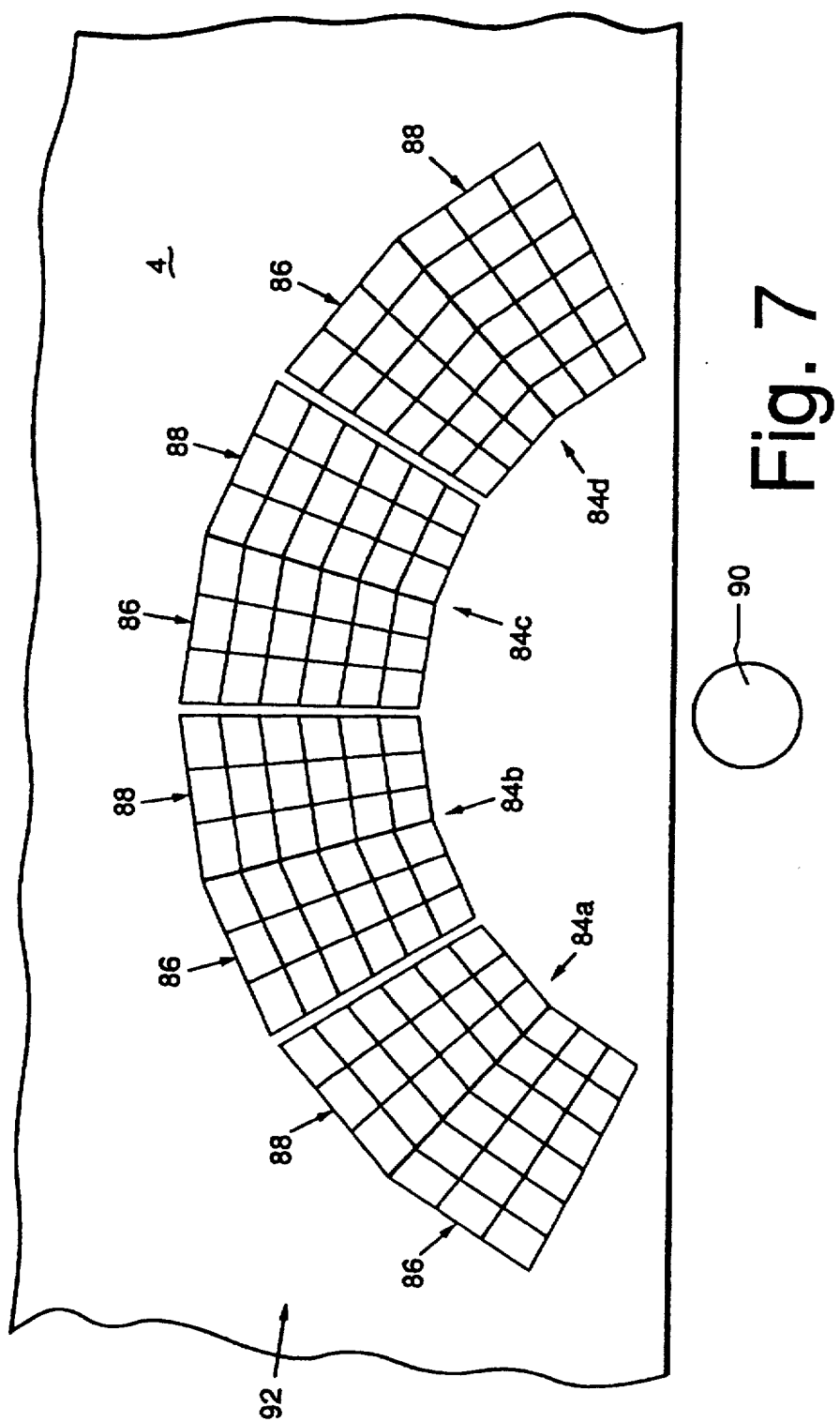
FIG. 7 is a plan view depicting a system of adjoined storage containers of FIG. 5 arranged in a generally semi-circular configuration about a user.

FIG. 7 is a plan view showing adjoined inclinable storage containers 84a-84d arranged, in a semi-circular fashion, around a user 90. In this embodiment, the containers 84a-84d form a container system 92 that provides a multitude of storage compartments within easy access of the user. It is envisioned that the production efficiency and speed of the user 90 will be greatly increased thereby increasing the user's 90 overall throughput.

Although the present invention has been described in terms of a specific embodiment and two alternate embodiments, it is anticipated that alterations and modifications thereof will no doubt become apparent to those skilled in the art. It is therefor intended that the following claims be interpreted as covering all such alterations and modifications as filed in the true spirit and scope of the invention.

What is claimed is:

1. An inclinable compartmented storage container disposed on a generally flat surface, said container for storing powder-like substances and the like used in the preparation of dental appliances, comprising:
    a) a flat, generally trapezoidally-shaped bottom plate having two parallel peripheral edges of non-equal length, and two non-parallel peripheral edges of equal length, a first midpoint associated with a first parallel edge and a second midpoint associated with a second parallel edge, said first midpoint and said second midpoint defining a line segment therebetween such that said line segment is perpendicular to each of said first parallel edge and said second parallel edge;
    b) an upstanding sidewall portion attached to each of said non-parallel edges, and extending generally upwards therefrom;
    c) an upstanding endwall portion attached to each of said parallel edges and extending generally upwards therefrom;
    d) means for inclining said container from said surface, said inclining means attached to said bottom plate and being positionable between a first position such that said container is inclined at an incline angle value from said surface, and a second position such that said container is disposed flush atop said surface;
    e) means for dividing the interior of said container into a plurality of non-rectangular quadrilaterally-shaped compartments of unequal volumes, each of said compartments including
        i) a base portion having a distal edge and a proximal edge, said base portion being inclined such that when said container is inclined, said base portion is substantially parallel to said surface, and when said container is flush atop said surface, said base portion is inclined at said incline angle value from said surface,
        ii) an inclined front wall portion attached to said distal edge of said base portion and extending generally obtusely upwards therefrom,
        iii) an inclined rear wall portion attached to said proximal edge of said base portion and extending generally obtusely upwards therefrom into attachment with an inclined front wall portion of another rearwardly adjacent compartment such that an adjoined rear wall portion and front wall portion form an inverted V.

2. An inclinable compartmented storage container as recited in claim 1, said container further comprising a rotatable lid attached to one of said upstanding endwall portions and including a tray covering portion having a shape generally identical to the trapezoidal shape of said bottom plate.

3. An inclinable compartmented storage container as recited in claim 2, wherein said inclining means includes
    a hinge attached to said bottom plate and disposed generally adjacent to and parallel to the longer of said parallel and edges of said bottom plate; and
    a rotatable support member attached to said hinge and rotatable between said first position and said second position.

4. An inclinable compartmented storage container as recited in claim 3, said container further comprising a means for identifying the substance contained in each of said compartments, said identification means including
    a base portion attached to an inclined rear wall portion associated with each of said compartments, said base portion having a notch formed therein; and
    label means for identifying the substance contained in said compartment, said label means being insertable into said notch of said base portion.

5. An inclinable compartmented storage container comprising:
    a) a flat, generally trapezoidally-shaped bottom plate having two parallel peripheral edges of non-equal length, and two non-parallel peripheral edges of equal length, a first midpoint associated with a first parallel edge and a second midpoint associated with a second parallel edge, said first midpoint and said second midpoint defining a line segment therebetween such that said line segment is perpendicular to each of said first parallel edge and said second parallel edge;
    b) an upstanding sidewall portion attached to each of said non-parallel edges, and extending generally upwards therefrom;
    c) an upstanding endwall portion attached to each of said parallel edges and extending generally upwards therefrom;
    d) means for inclining said container from said surface, said inclining means attached to said bottom plate and being positionable between a first position such that said container is inclined at an incline angle value from said surface, and a second position such that said container is disposed flush atop said surface;
    e) means for dividing the interior of said container into a plurality of non-rectangular quadrilaterally-shaped compartments of unequal volumes, each of said compartments including
        i) a base portion having a distal edge and a proximal edge, said base portion being inclined such that when said container is inclined, said base portion is substantially parallel to said surface, and when said container is flush atop said surface, said base portion is inclined at said incline angle value from said surface,
        ii) an inclined front wall portion attached to said distal edge of said base portion and extending generally obtusely upwards therefrom,
        iii) an inclined rear wall portion attached to said proximal edge of said base portion and extending generally obtusely upwards therefrom into attachment with an inclined front wall portion of another rearwardly adjacent compartment such that an adjoined rear wall portion and front wall portion form an inverted V.

6. An inclinable compartmented storage container as recited in claim 5, said container further comprising a rotatable lid attached to one of said upstanding endwall portions and including a tray covering portion having a shape generally identical to the trapezoidal shape of said bottom plate.

7. An inclinable compartmented storage container as recited in claim 6, wherein said inclining means includes
    a hinge attached to said bottom plate and disposed generally adjacent to and parallel to the longer of said parallel and edges of said bottom plate; and a rotatable support member attached to said hinge and rotatable between said first position and said second position.

8. An inclinable compartmented storage container as recited in claim 7, said container further comprising a means for identifying a substance contained in each of said compartment of said container, said identification means including a base portion attached to an inclined rear wall portion associated with each of said compartments, said base portion having a notch formed therein; and label means for identifying the substance contained in said compartment, said label means being insertable into said notch of said base portion.

9. An adjoined inclinable compartmented storage container disposed on a generally flat surface, having two individual inclinable compartmented storage containers attached to one another, each of said individual storage containers comprising:

a) a flat, generally trapezoidally-shaped bottom plate having two parallel peripheral edges of non-equal length, and two non-parallel peripheral edges of equal length, a first midpoint associated with a first parallel edge and a second midpoint associated with a second parallel edge, said first midpoint and said second midpoint defining a line segment therebetween such that said line segment is perpendicular to each of said first parallel edge and said second parallel edge;

b) an upstanding sidewall portion attached to each of said non-parallel edges, and extending generally upwards therefrom;

c) an upstanding endwall portion attached to each of said parallel edges and extending generally upwards therefrom;

d) means for inclining said container from said surface, said inclining means attached to said bottom plate and being positionable between a first position such that said container is inclined at an incline angle value from said surface, and a second position such that said container is disposed flush atop said surface;

e) means for dividing the interior of said container into a plurality of non-rectangular quadrilaterally-shaped compartments of unequal volumes, each of said compartments including i) a base portion having a distal edge and a proximal edge, said base portion being inclined such that when said container is inclined, said base portion is substantially parallel to said surface, and when said container is flush atop said surface, said base portion is inclined at said incline angle value from said surface, ii) an inclined front wall portion attached to said distal edge of said base portion and extending generally obtusely upwards therefrom, iii) an inclined rear wall portion attached to said proximal edge of said base portion and extending generally obtusely upwards therefrom into attachment with an inclined front wall portion of another rearwardly adjacent compartment such that an adjoined rear wall portion and front wall portion form an inverted V.

10. An adjoined inclinable compartmented storage container as recited in claim 9, each of said individual storage containers further comprising a rotatable lid attached to one of said upstanding endwall portions and including a tray covering portion having a shape generally identical to the trapezoidal shape of said bottom plate.

11. An adjoined inclinable compartmented storage container as recited in claim 10, wherein said inclining means includes a hinge attached to said bottom plate and disposed generally adjacent to and parallel to the longer of said parallel and edges of said bottom plate; and a rotatable support member attached to said hinge and rotatable between a first position and a second position.

12. An adjoined inclinable compartmented storage container as recited in claim 11, each of said individual storage containers further comprising a means for identifying the substance contained in each of said compartments, said identification means including a base portion attached to an inclined rear wall portion associated with each of said compartments, said base portion having a notch formed therein; and label means for identifying the substance contained in said compartment, said label means being insertable into said notch of said base portion.

label means for identifying the substance contained in said compartment, said label means being insertable into said notch of said base portion.

* * * * *